US00PP17391P2

(12) United States Plant Patent
Radler

(10) Patent No.: US PP17,391 P2
(45) Date of Patent: Jan. 30, 2007

(54) CLIMBING ROSE PLANT NAMED 'RADBRITE'

(50) Latin Name: *Rosa hybrida*
Varietal Denomination: Radbrite

(75) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 19 days.

(21) Appl. No.: 11/209,786

(22) Filed: Aug. 24, 2005

(51) Int. Cl.
*A01H 5/00* (2006.01)

(52) U.S. Cl. ..... Plt./109

(58) Field of Classification Search ..... Plt./109, Plt./114, 113
See application file for complete search history.

*Primary Examiner*—Kent Bell
*Assistant Examiner*—June Hwu
(74) *Attorney, Agent, or Firm*—Buchanan Ingersoll & Rooney PC

(57) ABSTRACT

A new and distinct variety of climbing rose plant is provided which forms in abundance on a nearly continuous basis attractive single blossoms that are salmon-pink with a yellow eye. The vegetation is vigorous and the growth habit is upright and climbing. Attractive ornamental satiny green foliage is formed. Excellent disease resistance to blackspot is displayed. The hardiness of the new variety is excellent for a climber. The new variety is particularly well suited for growing as distinctive ornamentation in the landscape.

1 Drawing Sheet

Botanical/commercial classification: *Rosa hybrida*/ Climbing Rose Plant.
Varietal denomination: cv. RADBRITE.

SUMMARY OF THE INVENTION

The new variety of *Rosa hybrida* climbing rose plant of the present invention was created at Greenfield, Wis., U.S.A. by artificial pollination wherein two parents were crossed which previously had been studied in the hope that they would contribute the desired characteristics. The female parent (i.e., the seed parent) was the 'RADtee' variety (non-patented in the United States). The male parent (i.e., the pollen parent) of the new variety was the 'AUScot' variety (U.S. Plant Pat. No. 7,215). A 'AUScot' variety is marketed under the ABRAHAM DARBY trademark. The parentage of the new variety can be summarized as follows:

'RADtee'×'AUScot'.

The seeds resulting from the above pollination were sown and small plants were obtained which were physically and biologically different from each other. Selective study resulted in the identification of a single plant of the new variety.

It was found that the new variety of climbing rose plant of the present invention possesses the following combination of characteristics:

(a) abundantly forms attractive single blossoms that are salmon-pink with a yellow eye, (b) exhibits an upright and climbing growth habit;

(c) forms vigorous vegetation, (d) forms attractive ornamental green foliage with a satiny finish, (e) exhibits excellent resistance to blackspot, and (f) exhibits excellent resistance to cold.

The new variety displays good repeat blooming, and the winter hardiness is believed to be one of the best observed for a climbing rose plant. The growth is very vigorous and the canes commonly are of medium to heavy caliper for the class.

The new variety well meets the needs of the horticultural industry. It can be grown to advantage as attractive climber in parks, gardens, public areas, and in residential settings. It alternatively can be trimmed and grown as a compact rose bush in the absence of support. The new variety is particularly well suited for providing attractive ornamentation in the landscape. The salmon-pink blossoms contrast nicely with the satiny green foliage.

The new variety of the present invention can be readily distinguished from its ancestors. More specifically, the 'RADtee' variety is a shrub rose that forms non-fragrant blossoms having approximately 12 petals which are white with a pink edge, and the 'AUScot' variety forms very large very double blossoms that display a blend of pastel pink, yellow, white and orange coloration.

The new variety of the present invention also can be readily distinguished from other climbing rose plants, such as the 'Radsunsar' variety (U.S. Plant Pat. No. 16,611) and the 'Wekroalt' variety (U.S. Plant Pat. No. 11,518), following an inspection of the blossom coloration. More specifically, the 'Radsunsar' variety forms blossoms that are entirely yellow, and the blossoms of the 'Wekroalt' variety are velvety red striped with white.

The characteristics of the new variety have been found at Waso, Calif. U.S.A., to be homogeneous and stable and are strictly transmissible by asexual propagation such as budding, grafting, and the rooting of cuttings from one generation to another. The new variety reproduces true to type by such asexual propagation.

The new variety has been named 'RADBRITE'.

BRIEF DESCRIPTION OF THE PHOTOGRAPH

The accompanying photograph shows, as nearly true as it is reasonably possible to make the same in a color illustration of this character, a typical flowering plant of the new variety while growing with support. The illustrated rose plant of the new variety was approximately three years of age and was observed during the summer while growing outdoors on its own roots at Greenfield, Wis. U.S.A.

DETAILED DESCRIPTION

The chart used in the identification of colors is that of The Royal Horticultural Society (R.H.S. Colour Chart), London, England. The description is based on the observation of three year-old specimens of the new variety during June while growing outdoors on their own roots near West Grove, Pa., U.S.A.

Class: Climbing Rose.

Plant:

*Height.*—Approximately 4 to 5 feet on average at the end of one growing season. The mature height is approximately 8 feet.

*Width.*—Approximately 3 to 4 feet on average at the end of one growing season. The mature width is approximately the same.

*Habit.*—Upright and climbing.

Branches:

*Color.*—Young stems: commonly between Green Group 139B and Yellow-Green Group 144A, and sometimes lightly blushed with between Greyed-Purple Group 183B and Greyed-Purple Group 187B when exposed to the sun. Adult wood: near Yellow-Green Group 148A.

*Texture.*—Young stems: smooth. Adult wood: smooth.

*Thorns.*—Size: on young stems several large almost straight prickles that are approximately 0.9 to 1.3 cm in length having a somewhat narrow moderately long base that is approximately 8 mm in length and approximately 5 mm in width commonly are present together with a few small prickles, and on mature wood similar large prickles commonly are present together with a few small prickles. Color: on young stems commonly between Greyed-Yellow Group 161A and Greyed-Orange Group 164B and often lightly suffused with Greyed-Red Group 181A and Greyed Purple Group 184B, and an adult wood commonly between Greyed-Orange Group 164A and Greyed-Orange Group 165A.

Leaves:

*Stipules.*—Approximately 20 to 25 mm in length, approximately 8 mm in width at the widest area, Green Group 138A in coloration, and possess moderately narrow medium to long points that commonly turn out at an angle of more than 45 degrees.

*Petioles.*—Approximately 37 mm in length on average, approximately 2 mm in diameter on average, slightly bristly in texture, and Green Group 138A in coloration.

*Rachis.*—Average in caliper, the upper side is moderately grooved with some stipitate glands and hairs at the edges of the groove, and the under side is somewhat rough with a few stipitate glands and numerous small prickles.

*Leaflets.*—Number: 3, 5, and 7. Shape: oval to somewhat ovate, rounded base, acute to somewhat acuminate tip. Margins: serrulate. Texture: semi-glossy and moderately rugose. Leaflet size: commonly approximately 4 to 5 cm in length on average and approximately 3 to 4 cm in width on average at the widest point. Leaf size: commonly approximately 9.5 to 14.5 cm in length on average and approximately 10.5 cm in width on average at the widest point. Overall appearance: very abundant, and medium green in coloration, with a semi-glossy finish. Color (young foliage): upper surface: commonly between Green Group 139A and Yellow-Green Group 147A and sometimes lightly suffused with near Greyed-Purple Group 183B and Greyed-Purple Group 187C. Under surface: Commonly between Green Group 139C and Yellow-Green Group 147B and moderately suffused with near Greyed-Purple 183B and Greyed-Purple Group 187C. Color (adult foliage): upper surface: commonly between Green Group 139A and Yellow-Green Group 147A. Under surface: commonly between Yellow-Green Group 147B and 147C.

Inflorescence:

*Number of flowers.*—Commonly approximately 4 to 5 blooms on average in a cluster. Commonly the clusters are irregularly rounded and are borne on medium to long stems having a length of approximately 20 to 30 cm.

*Peduncle.*—Commonly between Yellow-Green Group 144B and 144C and sometimes moderately suffused with near Greyed-Purple Group 183B and 183C, very strong, usually erect, smooth, with stipitate glands and hairs, and approximately 3 mm in diameter.

*Sepals.*—Approximately 25 mm in length, approximately 10 mm in width, commonly without extensions, the inner surface is lined with very fine wooly tomentum, the margins are lined with a few stipitate glands and hairs, the apex is acute, and Yellow-Green Group 144A fading to Yellow-Green Group 144C in coloration. Number: five.

*Buds.*—Shape: very pointed to urn-shaped as the calyx breaks. Length: approximately 2 to 3 cm on average as the calyx breaks. Width: approximately 2 to 2.5 cm at the widest point as the calyx breaks. Size: small to medium. Texture: bears numerous stipitate glands together with some hairs. Color: commonly between Yellow-Green Group 144A and 144B and moderately suffused with near Greyed-Purple Group 183B and 183C.

*Flower.*—Form: single to semi-double. Shape: when partially opened very high-centered with the petals being somewhat loosely spiraled and the petal edges somewhat slightly reflexed outward, and when fully opened somewhat flat and the petal edges are flat to undulated and very slightly reflexed outward. Diameter: approximately 10 to 11 cm. on average when fully open. Color (when opening begins): upper surface: at the apex near Red-Purple Group 58A and Red-Purple Group 59D, Yellow Group 3A and 3B near the base, and at the point of attachment Yellow-Group 7A. The yellow coloration towards the base of each petal creates a yellow eye at the center of each bloom when fully open. Under surface: at the apex near Red-Purple Group 58A and Red-Purple Group 59D, and thereafter Yellow Group 3A and 3B. Color (when blooming): upper surface: at the apex primarily Red Group 55B, and at the area of attachment a moderately large zone of Yellow Group 2A. Under surface: at the apex a blend of Red Group 52D and Red Group 55D, and at the area of attachment a moderately large zone of the Yellow Group 2C and Yellow Group 4D. Color (at end of blooming): upper surface: at the apex primarily Red Group 55A, and at the area of attachment a moderately large zone of Yellow Group 4D. Under surface: at the apex a blend of Red Group 55C and 55D, and at the area of attachment a moderately large zone of Yellow Group 11D. Fragrance: strong citrus-rose. Petal form: nearly round to very broadly obovate commonly with rounded apices, and sometimes notched with one or two notches. Petal size: commonly approximately 50 to 55 mm in length and width. Petal number: approximately 8 to 12 on average. Petaloids: commonly 1 to 2 arranged irregularly, approximately 34 mm in length, approximately 11 mm in width, and Yellow Group 7A in coloration. Texture: the petals are medium to thick in substance, the upper surfaces are moderately velvety to slightly satiny, and the under surfaces are mostly satiny to somewhat shiny. Lasting quality: blossoms commonly last approximately 4 to 5 days on the plant, and approximately 4 to 5 days when cut and placed in a vase depending upon environmental conditions. Petal drop: very good, the petals drop cleanly and freely Stamen number: approximately 165 to 170 on average and regularly arranged about the pistils. Anthers: commonly between Yellow Group 13C and Yellow-Orange Group 16A when immature, between Greyed-Orange Group 163A and Greyed-Orange Group 165A when mature, and approximately 1 mm in size. Filaments: approximately 7 to 12 mm in length on average, most bear anthers, and Yellow Group 13C and sometimes moderately suffused with Red Group 43C in coloration. Pollen: moderate to abundant in quantity and near Yellow Group 13B in coloration. Pistils: separate and free, and commonly number, approximately 50 on average. Stigmas: between Yellow Group 8D and Yellow Group 9D in coloration. Styles: moderately uneven in length, approximately 4.5 mm in length on average, approximately 0.25 mm in diameter, and near Yellow Group 8D and suffused with Red Group 46D in coloration. Receptacle: substantially round in configuration; commonly approximately 7 mm in diameter on average, commonly bears a somewhat bristly surface texture, and the coloration is Yellow-Green Group 144B. Ovaries: commonly enclosed in the calyx. Hips: ovoid to globular in shape, commonly approximately 18 mm in length on average and approximately 15 mm in width on average, possess a smooth surface with thick fleshy walls, the sepals commonly persist, and between Orange Group 28A and Orange-Red Group 33A in coloration. Seeds: commonly approximately 7 to 11 medium-sized seeds are formed per hip.

Development:

*Vegetation.*—Vigorous.

*Blossoming.*—Very abundant and nearly continuous during the growing season.

*Resistance to diseases.*—Excellent with respect to blackspot and powdery mildew when compared to other commercial varieties under comparable growing conditions new West Grove, Pa., U.S.A.

*Propensity to form hips.*—Good.

I claim:

1. A new and distinct climbing rose plant characterized by the following combination of characteristics:

(a) abundantly forms attractive single blossoms that are salmon-pink with a yellow eye, (b) exhibits an upright and climbing growth habit, (c) forms vigorous vegetation, (d) forms attractive ornamental green foliage with a satiny finish, (e) exhibits excellent resistance to blackspot, and (f) exhibits excellent resistance to cold;

substantially as herein shown and described.

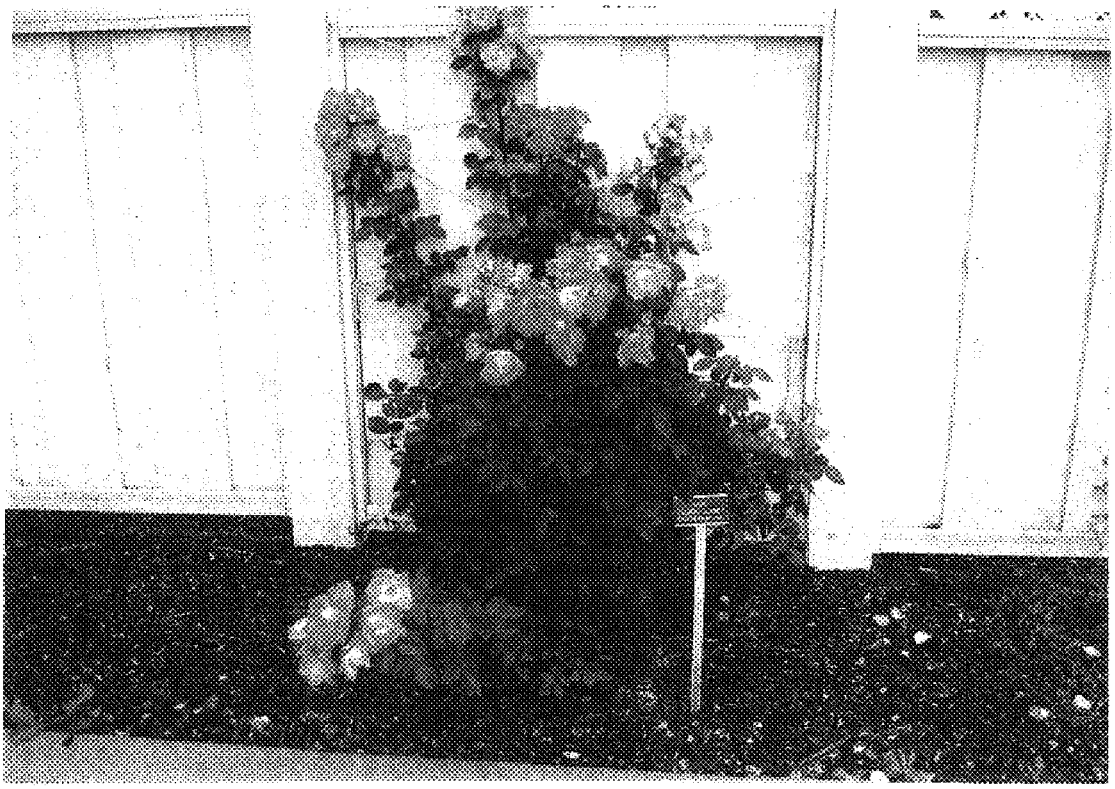

* * * * *